(12) United States Patent
Ostrovsky et al.

(10) Patent No.: US 7,837,682 B2
(45) Date of Patent: *Nov. 23, 2010

(54) DEVICE AND METHOD FOR POSITIONING OF A THERAPEUTIC DEVICE

(75) Inventors: Isaac Ostrovsky, Wellesley, MA (US); Ty Fairneny, Brighton, MA (US); Victor Shukhat, Canton, MA (US); Alfred Intoccia, Nashua, NH (US); Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1030 days.

This patent is subject to a terminal disclaimer.

(21) Appl. No.: 11/397,519

(22) Filed: Apr. 4, 2006

(65) Prior Publication Data

US 2006/0224037 A1   Oct. 5, 2006

Related U.S. Application Data

(60) Provisional application No. 60/667,968, filed on Apr. 4, 2005.

(51) Int. Cl.
*A61B 18/18* (2006.01)
*A61B 18/14* (2006.01)

(52) U.S. Cl. .................. 606/41; 600/29; 600/587; 600/591; 601/3; 606/2; 606/27; 606/32

(58) Field of Classification Search .............. 600/1, 600/2, 6, 11, 29, 30; 128/898, 899
See application file for complete search history.

(56) References Cited

U.S. PATENT DOCUMENTS 4,813,429 A * 3/1989 Eshel et al. ............... 600/549
(Continued)

FOREIGN PATENT DOCUMENTS

WO   03/011158   2/2003
(Continued)

*Primary Examiner*—Charles A Marmor, II
*Assistant Examiner*—Catherine E. Burk
(74) *Attorney, Agent, or Firm*—Fay Kaplun & Marcin, LLP

(57) ABSTRACT

A system comprises a first signal handling unit sized and shaped for insertion to a reference distance within a first body cavity and a probe sized and shaped for insertion into a second body cavity the probe including an energy emitting head and a second signal handling unit, wherein one of the first and second signal handling units comprises a transmitter and the other of the first and second signal handling units comprises one of a receiver adapted to receive signals from the transmitter and a signal reflecting element, wherein, when the other of the first and second signal handling units comprises a signal reflecting element, the one of the first and second signal handling units comprises a receiver in combination with a controller operatively connected to the receiver, the controller generating an output varying as a distance between the first and second signal handling units varies. In addition, a system comprises a probe sized and shaped for insertion in a first body cavity and a measuring element extending from the probe to contact tissue adjacent to an opening to a second body cavity, the measuring element being movably coupled to the probe to vary a depth to which the probe may be inserted into the first body cavity before the measuring element contacts the tissue adjacent to the opening of the second body cavity.

4 Claims, 4 Drawing Sheets

U.S. PATENT DOCUMENTS

| | | | | |
|---|---|---|---|---|
| 5,234,004 A | * | 8/1993 | Hascoet et al. | 607/116 |
| 5,800,378 A | * | 9/1998 | Edwards et al. | 604/22 |
| 5,941,251 A | * | 8/1999 | Panescu et al. | 128/899 |
| 6,142,959 A | * | 11/2000 | Sarvazyan et al. | 600/587 |
| 6,607,525 B2 | * | 8/2003 | Franco | 606/14 |
| 2002/0151767 A1 | * | 10/2002 | Sonnenschein et al. | 600/117 |
| 2003/0144576 A1 | * | 7/2003 | Presthus et al. | 600/29 |
| 2004/0236177 A1 | | 11/2004 | Matlock | |

FOREIGN PATENT DOCUMENTS

WO    WO 2004002319 A2 *    1/2004

* cited by examiner

US 7,837,682 B2

DEVICE AND METHOD FOR POSITIONING OF A THERAPEUTIC DEVICE

PRIORITY CLAIM

The present invention claims the benefit of U.S. Provisional Patent Application No. 60/667,968 entitled "Device and Method for Positioning a Therapeutic Device" filed Apr. 4, 2005, the entire disclosure of which is expressly incorporated herein by reference.

FIELD OF INVENTION

The present invention generally relates to medical apparatus and treatment methods. Specifically, the present invention relates to methods and devices to accurately position medical implements in the human body. More particularly, the present invention describes an apparatus and method to treat urinary incontinence and, more particularly, stress incontinence with a vaginal probe.

BACKGROUND

Stress urinary incontinence (SUI) occurs when tissue supporting the pelvic floor no longer provides sufficient support to the bladder neck and urethra, particularly the proximal urethra. Because of this condition, the bladder pushes against the urethra. Pressure from the abdominal muscles (e.g. during such activities as laughing, sneezing, coughing, exercising or straining to lift objects) can then cause undesired urine emissions. Females whose pelvic floors have stretched due to, for example, childbirth, obesity, etc. are more likely to suffer from stress incontinence.

Several treatments for SUI are available, ranging from medications to surgical interventions. One minimally invasive treatment for SUI utilizes radio frequency (RF) energy delivered to tissue of the pelvic floor, specifically to the endopelvic fascia (EPF) which lies beneath the surface of the vaginal wall. The RF energy heats the tissue of the endopelvic fascia and causes the collagen in the tissue to denature, so that the fascia shrinks. When the fascia shrinks, it returns the bladder and urethra to a more natural position within the pelvis, reducing the symptoms of incontinence. Other types of energy may be used to heat the tissue, such as acoustic energy, laser energy, microwaves etc.

Procedures to treat the endopelvic fascia require the accurate placement of the energy source within the vaginal canal of the patient, to successfully heat the target tissue. More generally, there are many medical procedures where a probe or other 'medical implement is inserted into a body lumen or cavity, to achieve some therapeutic effect on the surrounding tissue. In all these procedures, it is important to be able to accurately place the probe or other device relative to the target tissue, without direct visualization of the device. This task may be made difficult because of the geometry of the lumen, or because of the lack of convenient reference points near the opening of the lumen.

SUMMARY OF THE INVENTION

In one aspect, the present invention is directed to a system comprising a first signal handling unit sized and shaped for insertion to a reference distance within a first body cavity and a probe sized and shaped for insertion into a second body cavity the probe including an energy emitting head and a second signal handling unit, wherein one of the first and second signal handling units comprises a transmitter and the other of the first end second signal handling units comprises one of a receiver adapted to receive signals from the transmitter and a signal reflecting element, wherein, when the other of the first and second signal handling units comprises a signal reflecting element, the one of the first and second signal handling units comprises a receiver in combination with a controller operatively connected to the receiver, the controller generating an output varying as a distance between the first and second signal handling units varies.

According to a further aspect, the present invention is directed to a system comprising a probe sized and shaped for insertion in a first body cavity and a measuring element extending from the probe to contact tissue adjacent to an opening to a second body cavity, the measuring element being movably coupled to the probe to vary a depth to which the probe may be inserted into the first body cavity before the measuring element contacts the tissue adjacent to the opening of the second body cavity.

DETAILED DESCRIPTION

Figure 1:
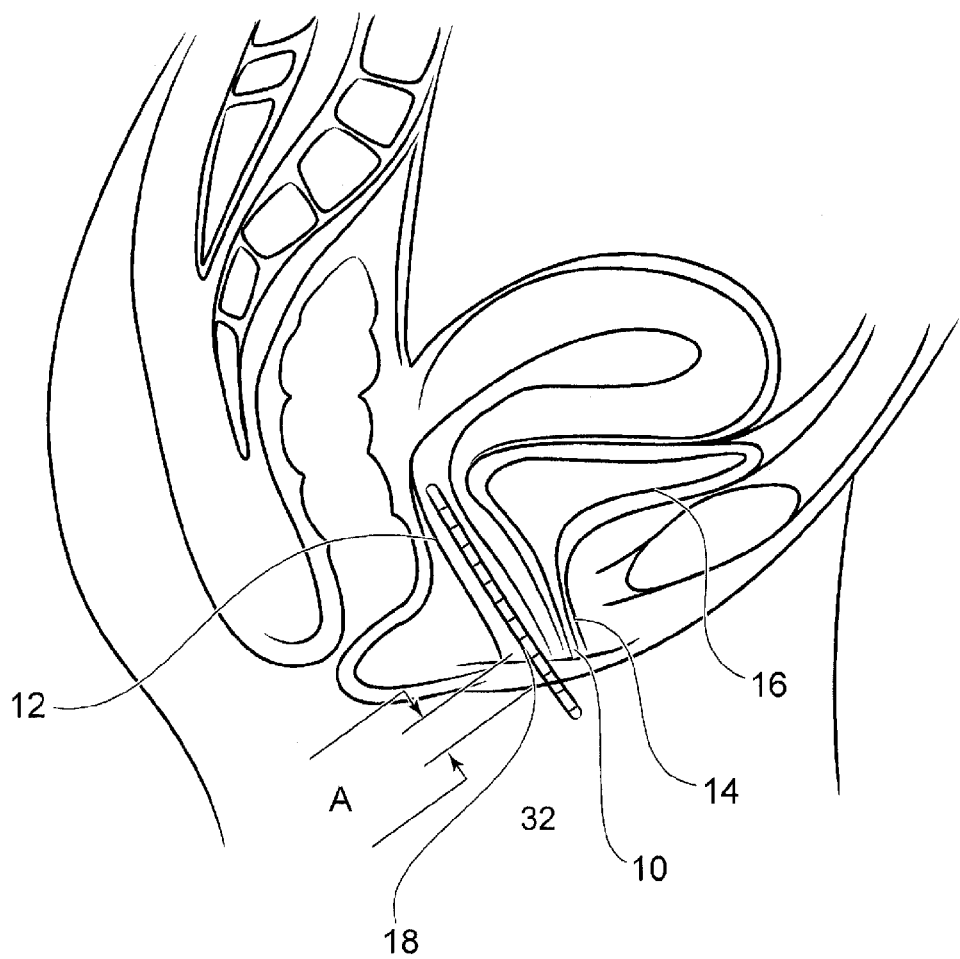
FIG. 1 is a cross-sectional diagram showing the anatomy of the female urinary and reproductive systems.

The present invention may be further understood with reference to the following description and the appended drawings, wherein like elements are referred to with the same reference numerals. The present invention is related to medical devices used to treat tissue adjacent to the walls of a body lumen or cavity, and to determine the position of the devices within the lumen. More specifically, the invention relates to a system for determining the position, relative to the urethra, of a device inserted into the vaginal canal for treatment of the endopelvic fascia.

Many medical procedures rely on inserting a medical implement into a body cavity or lumen of a patient, to carry out some therapeutic activity. For example, energy may be delivered from a probe into tissue surrounding the body cavity or lumen, to heat the tissue, to ablate portions of target tissue, or for other purposes. Energy may be delivered in the form of radio frequency energy, microwave energy, laser light, acoustic energy or any other appropriate form of energy. The location of the energy delivery probe within the lumen, in most cases, needs to be known so that the energy is delivered to the correct location to achieve the desired result. Direct visualization of the device, for example using fluoroscopy, may be used, however a simpler and less expensive way of determining the location of the device is often desirable.

One exemplary condition that can be alleviated by targeted delivery of energy is stress urinary incontinence (SUI). The treatment of SUI by altering the properties of the endopelvic fascia adjacent to the anterior vaginal wall and to the urethra is enhanced when the location on the endopelvic fascia of the tissue to be treated is precisely determined, and when treatment is accurately delivered to this location. However, difficulties in accurately treating a desired location may arise when the device for treating this tissue is inserted into the vaginal canal to a location determined with reference to a point along the urethra. This is often the case in treating SUI, because the location of the endopelvic fascia is typically determined along the urethra, but the therapeutic probe is inserted in the vagina.

For example, to ensure the safety and efficacy of procedures which treat the fascia by heating and shrinking it (e.g., through application of RF or ultrasound energy), accurately locating the device to deliver energy to the target tissue is important. For example, in these procedures, a location halfway between the urethral opening and the bladder neck may be chosen. This distance may be measured accurately by, for example, inserting a Foley catheter into the urethra to the bladder neck. However, difficulties arise when attempting to position a device within the vaginal canal adjacent to this accurately determined position. Specifically, although the vaginal canal is usually substantially parallel to the urethra, inserting a device into the vaginal canal to the measured distance determined from the urethra will not result in an accurate positioning of the device, as the opening to the vaginal canal 12 and the opening to the urethra 14 are in different planes as shown in FIG. 1. The amount of separation A between the two differs from patient to patient. In addition, as the opening to the vaginal canal 12 is not well defined, it is difficult to account for this separation A when positioning the device.

According to exemplary embodiments of the invention, a system is provided to determine the exact position of a medical probe within a body lumen or cavity, to place said probe at a predetermined location that maximizes the effectiveness of the treatment. The position sensing system allows the user, for example the physician performing the procedure, to place the probe in the desired location without using a direct visualization method such as fluoroscopy or an invasive surgical procedure. Instead, location of the probe is determined with reference to a nearby anatomical feature that is easier to determine than is location based on features of the lumen in which the probe is inserted.

In one exemplary embodiment, the probe comprises an ultrasound source that is used to treat SUI. During treatment, the probe is inserted into the vagina of the patient, and acoustic energy is generated and focused on the endopelvic fascia located beyond the wall of the vagina. The focused acoustic energy causes the fascia to contract, as described above, and brings about a reduction of the symptoms of incontinence. According to the invention, a transmitter and receiver pair is used to accurately and remotely locate the probe inside of the patient, and to specify the correct position where the probe should be placed to successfully carry out the procedure.

The ultrasound probe may be constructed, for example, as described in U.S. patent application Ser. No. 11/092,463, filed Mar. 29, 2005, entitled "Apparatus and Method for Stiffening Tissue", naming as inventors Isaac OSTROVSKY, Michael MADDEN, Jon T. McINTYRE and Jozef SLANDA, the entire disclosure of which is hereby expressly incorporated herein by reference. However, those skilled in the art will understand that the probe of the treatment apparatus may be any device used for performing a medical procedure on tissue. For example, the treatment device may be used for delivering RF energy to tissue, may be a needle for injecting material to or removing material from a desired location, may comprise an imaging device or any other device that must be located within the vaginal canal of the patient in a position referenced to the urethra. The treatment may also be applied to another body lumen or cavity, where positional reference is made with respect to a different cavity.

Treatment of SUI in female patients involves heating the endopelvic fascia that is attached to the urethra using a probe inserted into the vagina. The specific treatment location is dependent on the length and anatomical shape of the urethra. In general, the preferred location to place the probe and apply the energy approximately halfway along the length of the urethra, between the urethral meatus and the bladder neck. As shown in FIG. 1, the urethra 14 has a meatus 10 that is generally easy to recognize and to use as a reference for measurement purposes. The length of the urethra 14 between the meatus 10 and the bladder 16 may be used as the reference length to determine where to place the probe.

As described above, it is difficult to accurately determine a position within from the vaginal canal 12 corresponding to the target distance along the urethra 14. The variation in anatomy from one person to another is such that applying to the vaginal canal 12 a measurement derived form the urethra 14 can be very inaccurate leading to incorrect positioning of the probe. Numerous variations cause this inaccuracy. For example, the vaginal meatus 18 and the urethral meatus 10 may not lie in the same plane. The vagina 12 and urethra 14 may not be perfectly parallel, as seen in FIG. 1, and thus may have different internal distances between two adjoining points. In addition, the length of the urethra 14 varies from person to person, making standardized distances difficult to use. Because of these reasons, it is difficult to determine how far to insert the probe into the vaginal canal 12 to properly target the desired tissue.

The embodiments of the present invention allow the physician to measure the length of the urethra, and then insert in the vaginal canal the therapeutic energy delivery probe at the correct location with respect to the measured length. In a first step, the length of the urethra is measured, for example with a Foley catheter or with another measuring device suitable for the task. After measuring the length of the urethra, generally defined from the urethral meatus to the bladder, the physician determines the desired location for the treatment. Typically, the desired location to be treated is found at about half of the total measured length of the urethra.

Figure 2:
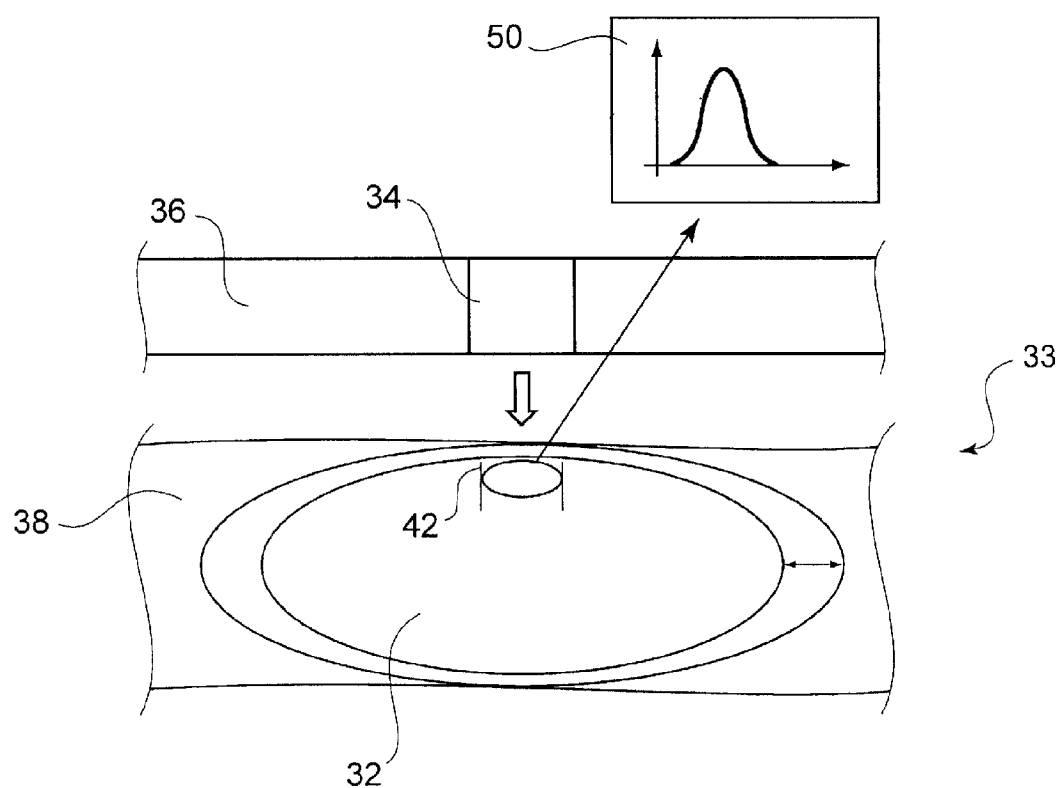
FIG. 2 is a schematic diagram showing an energy delivery device with a position sensing system according to a first embodiment of the present invention, in a desired position within the vaginal canal.

Once the desired location along the length of the urethra has been determined, the physician inserts into the urethra measuring element 33 including a transmitter 34, as shown in FIG. 2, via natural opening of the urethra. Conventional methods may be used to determine how far to insert the measuring element 33 to reach the desired reference location such as, for example referring to visible markers along the length of the measuring element 33 or a device such as a catheter attached thereto. A medical probe 32 is then inserted into the vaginal canal 38, through the vaginal opening. The probe 32 preferably comprises an energy source for heating and/or ablating the target tissue as desired for a particular application. For example, the probe 32 may comprise a source of acoustic energy such as ultrasound to heat target portions of the endopelvic fascia to treat SUI. A sensor 42 is placed in or on the probe 32, where it can sense the signal emanating from the transmitter 34. Those skilled in the art will understand that the transmitter 34 may be incorporated in the probe 32 with the receiver sensor 42 located in the measuring element 33 to achieve the same results described above. Alternatively, both the transmitter 34 and the receiver 42 may be located on the probe 32 with a signal reflecting element 43 incorporated into the measuring element 33.

In a different embodiment, the measuring element 33 is incorporated into a catheter or other similar device used to measure the length of the urethra 36. In this manner, after the length of the urethra 36 is determined, the catheter may be removed only partially to place the transmitter 34 in the desired location within the urethra 36. For example, distance markings may be placed externally on the catheter where they are visible to the physician, so that the transmitter 34 can easily be placed at the reference distance along the urethra 36 without using external measurement tools.

As the probe 32 is moved along the length of the vaginal canal 38, the receiver 42 senses the signal of the transmitter 34, and determines when the two components are closest to each other. For example, a processor 50 process a signal from the receiver 42 to generate an output which the user may interpret to determine when a selected location of the probe 32 has been reached—e.g., when the probe is closest to the transmitter 34. The output may be aural, visual or other as would be understood by those skilled in the art. For example, the display unit 54 may show a representation of the strength of the signal received by the receiver 42 from the transmitter 34. The closer the transmitter 34 and receiver 42 are, the stronger the signal is, as reported visually or aurally. Those skilled in the art will understand that when the receiver 42 is nearest to the transmitter 34, the probe 32 is at or nearly at a location corresponding to the reference position in the urethra 36. Alternatively, the processor may display a computed distance between the components. Alternatively, as would be understood by those skilled in the art, pulsed signals may be generated by the transmitter 34 with a propagation time of the pulses being used to determine a distance the signal travels between the transmitter 34 and the receiver 42.

The transmitter 34 and the receiver 42 may use any of a variety of energy sources and operating principles to determine the distance therebetween. For example, acoustic energy, electromagnetic energy or optical energy may be generated by the transmitter 34 and received by the sensor 42. Those skilled in the art will understand that as the probe 32 is moved within the vaginal canal 38, a point at which a strength of the energy received is a maximum, will correspond to a minimum distance that the energy has traversed through tissue and, consequently, to a minimum separation between the probe 32 and the target location. In one exemplary embodiment, a transmitter located in the patient's urethra and a receiver placed in the vaginal canal may be repeatedly positioned within about +/−2 mm from the point of minimal distance.

Once the probe 32 has been positioned in the desired reference location within the vaginal canal 38, the physician commences therapeutic treatment by, for example, applying energy from the probe 32 to heat the target tissue—e.g., target portions of the endopelvic fascia.

Figure 3:
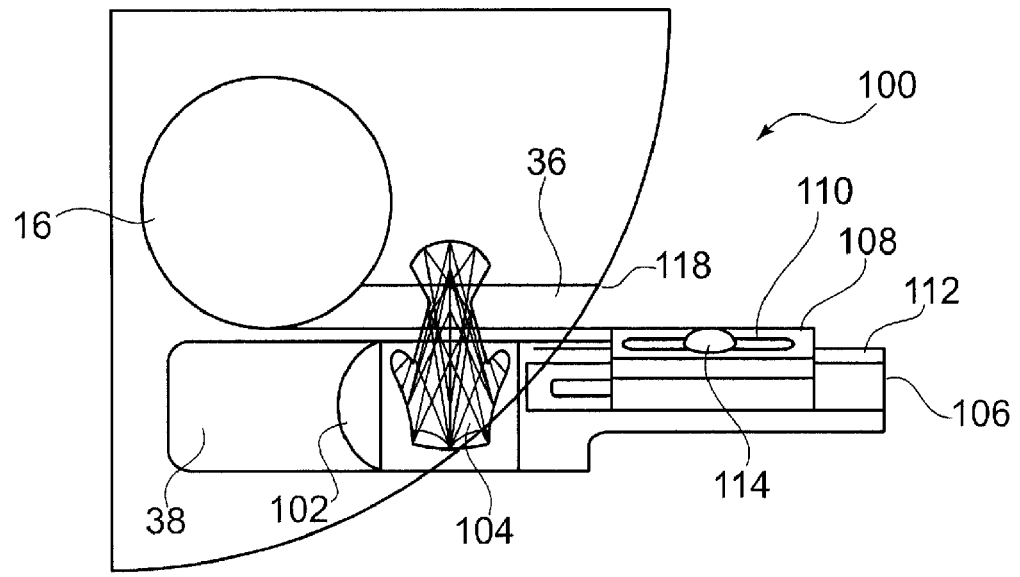
FIG. 3 is a diagram showing an energy delivery device with a position sensing system according to a second embodiment of the present invention.
Figure 4:
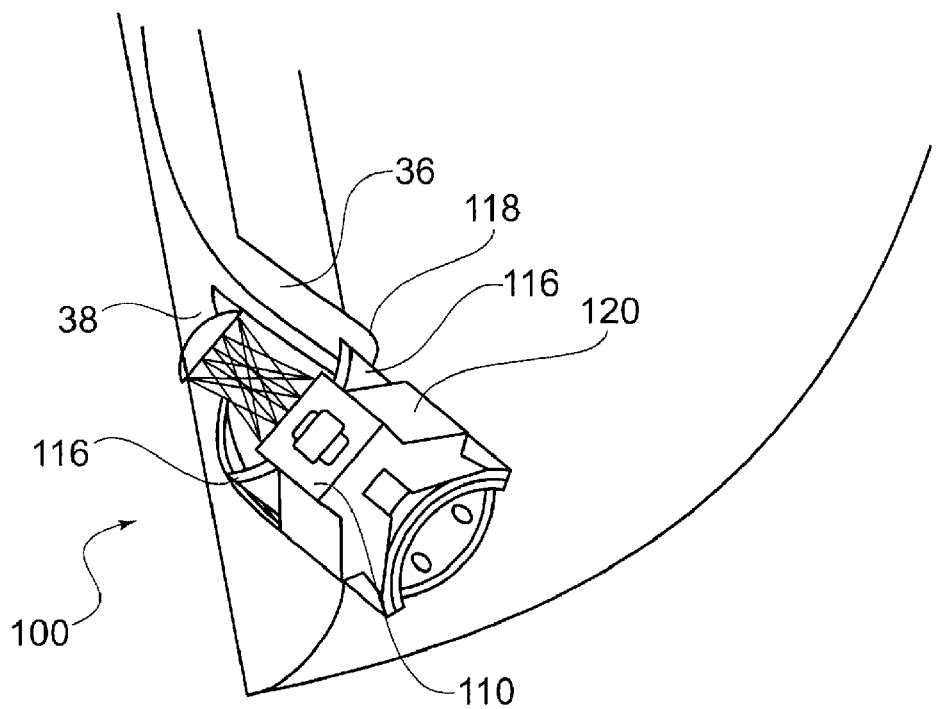
FIG. 4 shows a perspective view of the device shown in FIG. 3, in a desired position within the vaginal canal.

Another embodiment of the present invention utilizes a different principle to correctly position a therapeutic probe inside a body lumen or cavity. As shown in FIGS. 3 and 4, a device 100 for treating tissue near the vaginal canal 38 includes a distal, therapeutic head 102 housing a treatment apparatus (e.g., the ultrasound delivery unit 104) coupled to a proximal handle 106 with a positioning mechanism 108 mounted thereon. The positioning mechanism 108 includes a sliding stop member 110 mounted on the handle 106 for movement along a ridge 112, which is substantially parallel to an axis of the device 100. The mechanism also includes a locking screw 114 (or other locking mechanism) for fixing the stop member 110 in a desired position relative to the handle 106.

One specific embodiment of the treatment device according to the present invention provides a method of placing a treatment device within the vaginal canal 38, such that the urethral meatus 118 is used as the reference point for measuring the urethral length as well as for placement of the device. Procedures to treat SUI in particular may benefit from this embodiment of the invention. This method eliminates placement errors that may result from variability of the urethral length from one patient to another. Since the urethral meatus 118 is well defined physically, it is easily identified during the procedure. It can thus be used as a positive stop for the sliding measuring mechanism described above.

As shown in FIG. 4, the positioning mechanism 108 includes at least one abutting surface 116 extending from the stop member 110. In one exemplary embodiment, the device 100 according to the invention includes two abutting surfaces 116 formed on the stop member 110, on either side of the ridge 112. The angular positioning of the abutting surfaces 116 relative to the body of the probe or therapeutic head 102 may be selected so that, when the abutting surfaces 116 rest in contact with a portion of the patient's body adjacent to the urethral opening, the therapeutic head 102 is in an orientation appropriate to carry out the treatment of the target tissue. For example, the abutting surfaces 116 may be designed to rest on the urethral meatus, and use it as a reference point to measure the length of the urethra and to position the therapeutic head 102 in the vaginal canal 38.

Using two abutting surfaces 116 that are disposed symmetrically about the ridge 112 facilitates the targeting of two regions of target tissue disposed symmetrically about the urethra 36. This may be desirable, for example, in certain treatments for SUI, where regions of target tissue on both sides of the urethra 36 are treated. In a preferred embodiment, the abutting surfaces 116 are separated from a centerline of the therapeutic head 102 by a distance that is approximately equal to a distance between the openings of the vaginal canal 38 and of the urethra 36. In one embodiment, devices having a range of sizes may be provided with different separations between the abutting surfaces 116, to fit patients with different anatomies. Alternatively, a variety of conventional mechanisms may be employed to allow the user to vary this separation distance, preferably symmetrically by an equal amount for both abutting surfaces 116.

Figure 5:
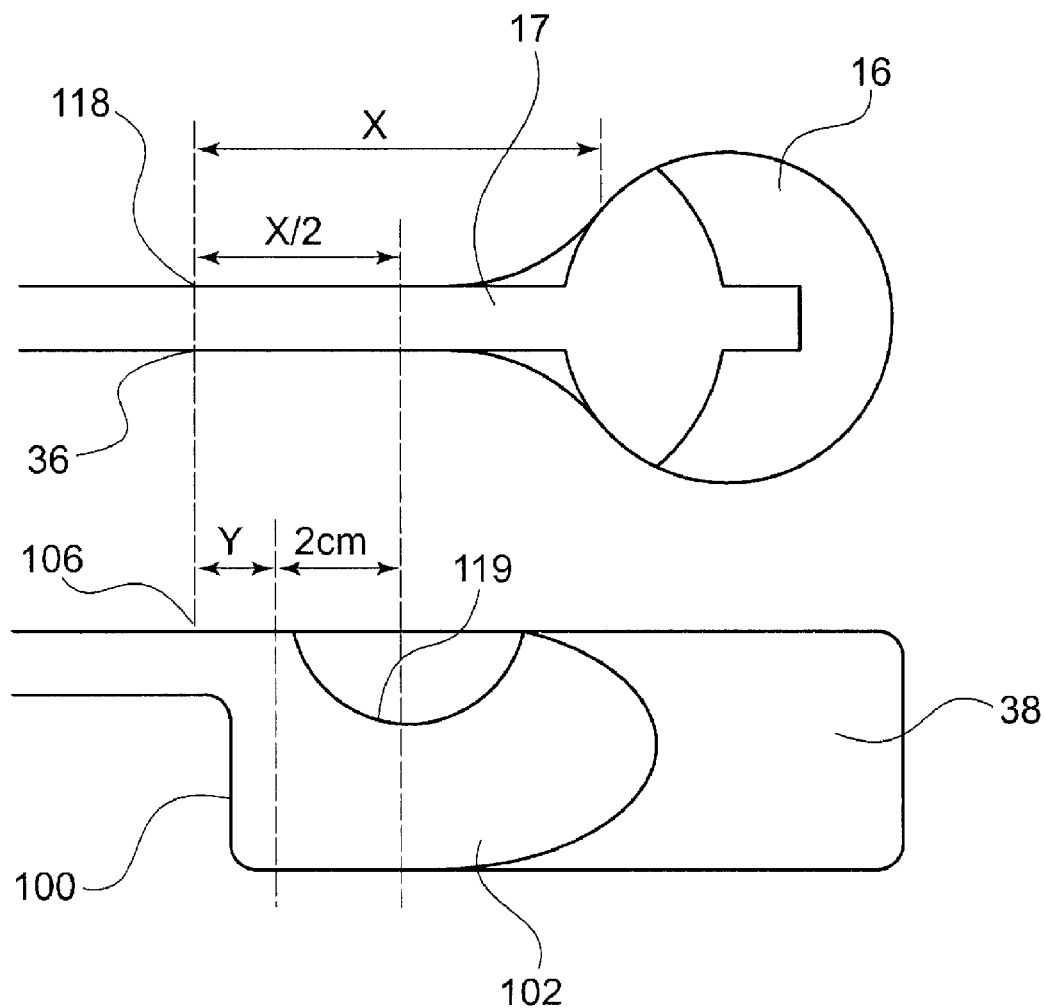
FIG. 5 illustrates the method for measuring a depth of insertion of the probe within the vaginal canal corresponding to a desired location along the urethra.

In normal use, as shown in FIG. 5, the physician performing the procedure with the device 100, begins by measuring the distance between the opening to the urethra 36 and the base of the bladder 16 using a Foley catheter 17 or similar device, as is known in the art. The urethral meatus 118 may be used as the reference point for the measurement. Depending on where the target tissue is located along the urethra 36, an appropriate percentage of the urethral length is used as the reference distance for treatment. For example, if the target portion of tissue is located halfway along the length X of the urethra 36, half of the total measured urethral length (X/2) becomes the reference distance for the treatment.

In a second step, the reference distance is measured from the treatment apparatus (e.g., a center of focus of energy projected by the ultrasound delivery unit 104) proximally along the device 100 to a stop position on the handle 106. The user then loosens the locking screw 114, slides the stop member 110 along the handle 106 until one or both of the abutting surfaces 116 are at the stop position and re-tightens the locking screw 114 to fix the stop member 110 and the abutting surfaces 116 in the desired position. As would be understood by those skilled in the art, detents or any other suitable mechanism may be substituted for the locking screw to maintain the stop member 110 and the abutting surfaces 116 in the desired position. A ruler or other type of measuring markings may be incorporated in the handle 106 to show, for example the distance between the sliding stop member 110 and the focal point of the delivered energy.

Once the reference distance is set with the stop member 110 and the locking screw 114, the user inserts the therapeutic head 102 into the vaginal canal 38, and orients at least one of the abutting surfaces 116 to align with the urethral opening or meatus. The therapeutic head 102 is then inserted in the vaginal canal 38 until one or both of the abutting surfaces 116 contacts the tissue surrounding the opening to the urethra 36. At this point a desired portion 119 of the therapeutic head 102 is positioned at a depth within the vaginal canal 38 that is substantially the same as the reference distance X/2, and is inserted at an angular orientation such that the energy generated is focused toward the target tissue.

If it is necessary to focus energy on different regions of target tissue around the vaginal canal, the therapeutic head 102 may be rotated using the handle 106. In this case the handle 106 may comprise two abutting surfaces 116 separated by a desired angle that cooperate with the sliding stop member 110. When the treatment is complete in a first orientation with a first one of the abutting members 116 contacting the urethral meatus 118, the device is turned by a predetermined angle using the handle 106, so that the second one of the abutting surfaces contacts the urethral meatus 118. The deposition of energy may then be carried out at the second location ensuring that the deposition of energy occurs at a desired angular orientation and at the reference axial distance.

In some procedures, it may be necessary to make more than one energy application at different axial distances within the vaginal canal 38 corresponding, for example, to points at different reference distances along the urethra 36. In this case, the sliding stop member 110 may be released and repositioned to the new distance, and the locking screw 114 may be again tightened. The probe's therapeutic head 102 is then inserted into the vaginal canal 38 until the abutting surfaces 116 abut the urethral meatus 118 at the new position and the application of energy is repeated.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. A method of treating tissue comprising:
   determining a depth of target tissue to be treated based on a depth within a first body cavity;
   adjusting a position of a measuring element of a probe so that a distance along an axis of the probe between a contacting surface of the measuring element and a treatment element of the probe substantially equals the depth of the target tissue within the first body cavity, wherein the measuring element includes a plurality of tissue contacting surfaces separated from one another by a desired angle, each tissue contacting surface defining a desired angular orientation of the probe within the second body cavity;
   locking a locking element in a desired position relative to the probe;
   advancing the probe into a second body cavity separate from the first body cavity until the contacting surface of the measuring element contacts tissue at an opening to the first body cavity, preventing further insertion of the probe into the second body cavity; and
   operating the treatment element.

2. The method according to claim 1, wherein the measuring element is slidably coupled to the probe.

3. The method according to claim 2, wherein the locking element is locked by tightening a locking screw.

4. The method according to claim 1, wherein the first body cavity is a urethra and the second body cavity is a vaginal canal.

* * * * *